(12) United States Patent
Burger-Kentischer et al.

(10) Patent No.: US 8,876,903 B2
(45) Date of Patent: Nov. 4, 2014

(54) IN VITRO TEST SYSTEM FOR VIRAL INFECTIONS

(75) Inventors: Anke Burger-Kentischer, Stuttgart (DE); Ina Hogk, Waiblingen (DE); Doris Finkelmeier, Fellbach (DE); Heike Walles, Sindelfingen (DE); Steffen Rupp, Stuttgart (DE); Michaela Kaufmann, Schwelm (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 531 days.

(21) Appl. No.: 13/151,343

(22) Filed: Jun. 2, 2011

(65) Prior Publication Data

US 2011/0300530 A1 Dec. 8, 2011

(30) Foreign Application Priority Data

Jun. 2, 2010 (DE) .................. 10 2010 023 156

(51) Int. Cl.
*A61F 2/10* (2006.01)
*G01N 33/50* (2006.01)

(52) U.S. Cl.
CPC ............ *G01N 33/5058* (2013.01); *A61F 2/105* (2013.01); *G01N 2333/035* (2013.01)
USPC ..................................................... 623/15.11

(58) Field of Classification Search
None
See application file for complete search history.

(56) References Cited

U.S. PATENT DOCUMENTS

| | | | |
|---|---|---|---|
| 5,755,814 A | 5/1998 | Berg et al. | |
| 5,888,248 A | 3/1999 | Berg et al. | |
| 5,945,101 A | 8/1999 | Berg et al. | |
| 5,955,343 A | 9/1999 | Holmes et al. | |
| 6,800,481 B1 | 10/2004 | Holmes et al. | |
| 2004/0023907 A1 | 2/2004 | Dieterich et al. | |
| 2004/0087013 A1 | 5/2004 | Holmes et al. | |
| 2007/0190603 A1 | 8/2007 | Holmes et al. | |
| 2010/0285086 A1 | 11/2010 | Lee et al. | |

FOREIGN PATENT DOCUMENTS

| | | | |
|---|---|---|---|
| WO | WO 99/04811 | * | 2/1999 |
| WO | WO 01/49827 | * | 7/2001 |
| WO | 01/92476 | | 12/2001 |
| WO | 2009/105130 | | 8/2009 |

OTHER PUBLICATIONS

Orgel, et al. Microfibrillar structure of type I collagen in situ, PNAS 2006; 103(24): 9001-9005.*
MacNeal, Structure and Function of the Skin in "The Merck Manual: Home Health Handbook" revised 2006; downloaded Jan. 10, 2014.*
Bernstein and Kappes, Enhanced in vitro reactivation of latent herpes simplex virus from neural and peripheral tissues with hexamethylenebisacetamide. Arch. Virol. 1988; 99:57-65.*

(Continued)

*Primary Examiner* — Zachariah Lucas
*Assistant Examiner* — Stuart W Snyder
(74) *Attorney, Agent, or Firm* — Harness, Dickey & Pierce, P.L.C.

(57) ABSTRACT

The invention relates to a multi-layered biological in vitro tissue containing: dermis layer, containing a collagen biomatrix with fibroblasts embedded therein and epidermis layer, containing epithelial cells. It is provided that latently virally infected neuronal cells are integrated at least into the dermis layer.

20 Claims, 7 Drawing Sheets

(56) References Cited

OTHER PUBLICATIONS

Moxley, et al. Herpes simplex virus type 1 infection prevents detachment of nerve growth factor-differentiated PC12 cells in culture. J. Gen. Virol. 2002; 83: 1591-1600.*

Wald, Genital HSV-1 infections. Sex. Transm. Infect. 2006; 82:189-190.*

Köllisch, et al. Various members of the Toll-like receptor family contribute to the innate immune response of human epidermal keratinocytes. Immunology, 2005; 114: 531-541.*

MacNeil Biomaterials for tissue engineering of skin. Materials Today, 2008; 11(5): 26-35.*

Scuderi, et al. The clinical application of autologous bioengineered skin based on a hyaluronic acid scaffold. Biomaterials. 2008; 29: 1620-1629.*

Ying-Hsiu Su et al., "Human Corneal Cells and Other Fibroblasts Can Stimulate the Appearance of Herpes Simplex Virus from Quiescently Infected PC12 Cells", Journal of Virology, May 1999, vol. 73, No. 5, pp. 4171-4180.

Christine Hoffman, "Charakteriseriung organotypischer Hautmodelle für In-vitro-Permeationsuntersuchungen" (Characterization of Organotypic Skin Construct for In-Vitro-Permeation Studies), from Dissertation approved by the Department of Life Sciences, Technische Universität Carolo-Wilhelmina, Braunschweig, Submitted to attain the degree of Doctorate of Natural Sciences, 2006, with English translation thereof.

Uroukov, I. S. et al: "Electrophysiological measurements in three-dimensional in viv-mimetic organotypic cell cultures: Preliminary studies with hen embryo brain spheroids", Neuroscience Letters, Limerick, IE, Bd. 404, n4. 1-2, Aug. 14, 2006 pp. 33-38, XP027885797, ISSN: 0304-3940.

European Search Report for parallel application EP 11004178, EPO/The Hague, mailed Jul. 13, 2012.

* cited by examiner

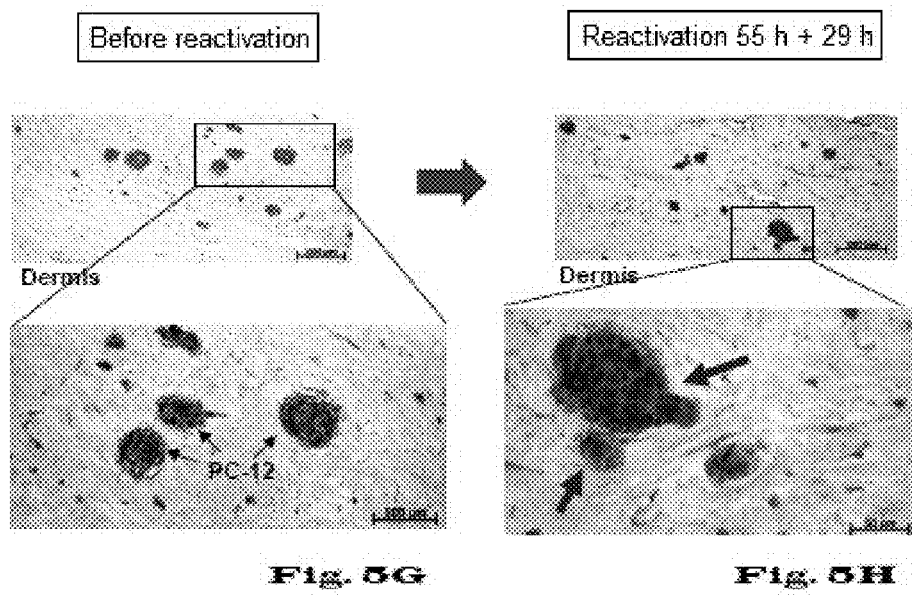

IN VITRO TEST SYSTEM FOR VIRAL INFECTIONS

CROSS-REFERENCE TO RELATED APPLICATIONS

This application claims the benefit and priority of DE 10 2010 023 156.8, filed Jun. 2, 2010. The entire disclosure of the above application is incorporated herein by reference.

FIELD

The invention relates to cell-based in vitro assays and test systems, in particular for examining viral infections and active ingredients with anti-viral action. It provides a multi-layered biological tissue as an in vitro test system for virus infections and substances with an anti-viral action. The invention also provides methods and means for finding an anti-viral active ingredient in an in vitro assay.

BACKGROUND

This section provides background information related to the present disclosure which is not necessarily prior art.

A multiplicity of infectious diseases in humans or animals are caused by viruses. Viruses do not have their own metabolism, which makes the causal treatment of viral infectious diseases difficult. In particular, they cannot be treated by antibiotics. Viricides that is, drugs that destroy viruses, are not currently available. Often a patient's immune system is not able to eradicate the infecting virus alone. Known substances with an antiviral action, so-called virustatics, prevent the spread or multiplication of viruses by various active mechanisms, which are connected with the infection cycle or multiplication cycle of the viruses. Known virustatics act in particular as DNA polymerase inhibitors. Known substances with nucleotide action are idoxuridine, aciclovir and ganciclovir and derivatives thereof. Other polymerase inhibitors are, for example, poscarnet and ribavirin.

Infections with the herpes simplex virus (HSV) are among the most common diseases in humans. More than 90% of the total world population are infected with this virus. Herpes simplex viruses (HSV) are divided into two closely related virus species (human herpes virus 1 (HSV1) and human herpes virus 2 (HSV2). The herpes viruses cause very different diseases of the herpes simplex, including herpes simplex encephalitis and neonatal herpes. The most widespread are herpes labialis and genital herpes.

A characteristic of HSV is persistence. After initial infection of the cells of the animal or human host organism, particularly of epithelial cells of the mucous membrane, the virus spreads into neuronal cells, in particular cells of sensory neurons, which innervate the primarily infected region. The viruses reach the ganglia via retrograde axonal transport and typically appear there in a latent state. The virus DNA persists, essentially unrecognized by the host's immune system, as a circular episome in the nucleus of the ganglia. During the latency phase, no virus replication takes place, the infected host is symptom-free. A reactivation of the latent viruses is triggered by stressors, such as a weakened immune system, exposure to sunlight, inflammatory events, hormonal or psychological effects (neuroendocrinological conditions) or nerve irritation. Virions thereby migrate axonally out of the ganglia back into the periphery and reinfect the tissue there, in particular the epithelial cells. The typical clinical picture of a herpes infection is shown by a lytic replication cycle in the epithelial tissue, and the tissue destruction resulting therefrom. The known therapy of a herpes infection is inadequate. Known virustatics can only relieve the symptoms and shorten the infection period but are not able to end the persistence of the viruses in the ganglia cells (eradication).

Many of the studies hitherto carried out on the latency mechanisms and reactivation analyses are obtained with the aid of mammalian cell lines. However, these test systems lack direct applicability to the in vivo situation in the patient. Consequently, animal experiments continue to be used in studies of the infection and latency mechanisms, but in particular in the development of active ingredients. It is desirable to develop in vitro test systems that permit a direct applicability of the results obtained thereby to the situation in the infected patient and that can replace animal studies.

With the aid of standardized three-dimensional in vitro skin equivalents, which are reconstituted from primary skin cells and/or skin cell lines, human skin can be reproducibly replicated. Physiologically such skin equivalents are largely comparable to native skin. As is known, they are used as in vitro tests systems for skin tissue (in vitro skin model).

SUMMARY

This section provides a general summary of the disclosure, and is not a comprehensive disclosure of its full scope or all of its features.

The technical problem on which the invention is based was to provide an in vitro test system, by means of which in particular latency mechanisms and reactivation analyses in virus infections, in particular with HSV infections, can be carried out and the results thereof can be applied in particular directly to the in vivo situation in a human or animal organism. In particular the in vitro test system should render possible a screening of active substances to find substances with an anti-viral action.

The technical problem is fully solved by the provision of a multi-layered biological in vitro tissue, that contains a dermis layer and preferably also an epidermis layer, wherein the dermis layer is essentially made up of a collagen biomatrix with fibroblasts embedded, that is, integrated, therein or containing them. The epidermis layer arranged thereon contains essentially epithelial cells, that is, in particular keratinocytes. Dermis layer and epithelial layer can form a model system that is similar or equivalent to human skin tissue. The in vitro test model according to the invention is based accordingly on an in vitro skin model. According to the invention, this multi-layered biological tissue is characterized above all in that at least in the dermis layer thereof, in addition to the fibroblasts, in particular virally infected, but in particular latently infected, neuronal cells are integrated.

Further areas of applicability will become apparent from the description provided herein. The description and specific examples in this summary are intended for purposes of illustration only and are not intended to limit the scope of the present disclosure.

In a special embodiment the viral infection of the neuronal cells is an active or reactivatable latent infection with the herpes simplex virus (HSV), in particular with the herpes simplex virus 1 (HSV1). However, the invention is not restricted to this virus type. In other preferred embodiments of the in vitro test system, the virus is selected from: CMV, VZV, HBV, influenza A, influenza B, RSV and HCV.

In a special embodiment, the neuronal cells embedded into the in vitro test system are the cell line of pheochromocytoma cells; in particular these are cells of type PC12 (pheochromocytoma 12).

The invention therefore provides above integrating preferably latently virally infected neuronal cells into a multi-layered, so-called three-dimensional in vitro skin equivalent in order to obtain a new kind of in vitro test system. Above all the progression and the mechanisms of a viral infection, that is, in particular the reactivation of a latent virus infection and the interaction of the infected neuronal cells with the skin cells can be tested therewith. This makes it possible compared to known test systems to carry out tests of this type more simply, more reliably and also more informatively, but in particular screenings for the purpose of finding and characterizing potential substances with anti-viral action.

In a special embodiment in the epidermis layer of the in vitro test system the epithelial cells are selected from cells of keratinocyte cell lines and/or primary keratinocytes. In a special variant thereof, the epithelial cells originate from the keratinocyte cell line HaCaT (human adult low calcium high temperature) or are cells derived therefrom. In particular HaCaT cells surprisingly show a differentiation behavior largely corresponding to the in vivo state of a skin tissue and can thus improve the applicability of the findings obtained by means of the in vitro test system according to the invention to the in vivo situation. Particularly in connection with an epidermis layer built up largely or exclusively of HaCaT cells or cells derived therefrom, it is provided that the in vitro tissue is cultivated in culture medium that contains at least one or more of the culture factors selected from TGF-$\alpha$, GM-CSF and IL-1$\alpha$. Such culture factors are suitable for further improving the approximation of the cell status to the in vivo situation.

In a special variant, the keratinocytes used to build up the epidermis layer are alternatively or additionally genetically modified: for the purpose of testing the signal paths in a virus infection, the keratinocytes are preferably deficient for one or more pattern recognition receptors (PRR), that is, they represent a knock down mutant or optionally a knock out mutant for receptors of this type. In a special variant, the deficient PRR is selected from the group of the toll-like receptors (TLR): TLR2, TLR5 and TLR9 are preferred. Accordingly, the invention in a special embodiment provides an in vitro test system, wherein the epidermis layer contains keratinocytes or is built up thereof, which are knock down mutants or knock out mutants for one or more TLR, in particular for TLR2, TLR5 and/or TLR9. In order to achieve this, in particular HaCaT cells with small interfering RNA (siRNA) for TLR coding plasmides can be transfected in a manner known per se (nucleofection, RNA interference, (RNAi) method). Through siRNA cellular proteins can be suppressed, that is, "knocked down" in a manner known per se. A complete suppression of the proteins does not need to be achieved; the invention does not require a complete suppression (knock out) in this embodiment. The invention is not restricted to this embodiment for producing a knock down mutant. The knock down mutants HaCaT$\Delta$TLR2, HaCaT$\Delta$TLR5 and HaCaT$\Delta$TLR9 and knock down combinations (double-mutants, multiple mutants) thereof are preferred. The invention is not limited to these knock down mutants.

In an alternative variant, the epidermis layer, additionally or exclusively, contains primary epithelial cells, which obtained in particular in preceding steps, from tissue of the oral mucosa or tissue comparable thereto from the intestine, gastric mucosa, skin, cornea, trachea and other epithelial tissues. A particular source of epithelial cells is represented by human donor tissue, in particular foreskin (prepuce).

In a special embodiment, the dermis layer of the in vitro test tissue is built up of a collagen biomatrix, which essentially contains type-I collagen or preferably is composed thereof. Type-I collagen is provided in a preferred variant as largely or essentially native collagen. To this end, in particular the collagen is extracted as freshly as possible and without denaturing interim steps from collagen-containing tissue, in particular from tissue rich in type-1 collagen, for example, rat tail sinews, lightly acetous, or alternatively extracted by means of urea and preferably brought to gelation by raising the pH value and/or by renaturing in buffer, in particular by the addition of buffered cell suspension, in order to obtain a collagen biomatrix, in particular with cells embedded therein, particularly fibroblasts, preferably with neuronal cells additionally embedded therein according to the invention, which forms the dermis layer. In the production/provision of the collagen biomatrix, preferably denaturing steps, such as salt precipitation, strong alkalinity or acidity, thermal denaturing as well as lyophilization are avoided or ruled out completely. In order to obtain a native collagen structure, the collagen-containing starting tissue is preferably extracted at low temperature with low acid concentration, in particular pH 4 or more, for a comparatively long time, in particular 3 or 4 days and gelated by dilution with buffer solution and/or by increasing the temperature, for example, at room temperature.

In a special variant, the dermis layer contains primary fibroblasts, preferably human primary fibroblasts. These are preferably obtained fresh from human donor tissue, for example, foreskin tissue. To this end, in a first step in the donor tissue the skin layers are separated and isolated fibroblasts are recultivated from the isolated dermis layer of the donor tissue and embedded in the collagen biomatrix, in order to form a reconstituted dermis layer.

In a further special embodiment, in addition, immunocompetent cells, that is, in particular immune cells, are integrated into the test tissue according to the invention. The significance of the in vitro test system based on the tissue according to the invention can be improved thereby. Still inactive epidermally located dendritic cells, particularly preferably Langerhans cells, are hereby preferred in particular. The immunocompetent cells are used in particular to support the intercellular communication in the test tissue, in that they process antigens and optionally can present further immune cells. The invention provides thereby that the immunocompetent cells are seeded on or in the dermis layer or are embedded therein together with the fibroblasts.

The subject matter of the invention is also a method for producing a multi-layered biological tissue, which can be used in particular as an in vitro test system, in particular for examining virus infections and/or for screening active ingredients with an anti-viral action. In a first process step, to produce a multi-layered base tissue, a collagen biomatrix is provided. This is preferably produced as described herein. Preferably, the collagen biomatrix contains essentially type-I collagen in non-denatured form or is composed thereof. According to the invention the fibroblast cells characterized in more detail elsewhere herein are embedded in the biomatrix. To this end, the fibroblasts are suspended in the not yet hardened gelated collagen solution: alternatively, the collagen solution is mixed with a suspension of fibroblasts in buffer and/or cell culture medium. The collagen biomatrix hardens with the fibroblasts suspended therein.

According to the invention, it is provided that in addition preferably virally infected neuronal cells, as are characterized in more detail elsewhere herein, are embedded in the dermis layer. The embedding of the neuronal cells is preferably carried out together with the embedding of the fibroblasts. To this end, fibroblasts as well as the preferably (latently) virally infected neuronal cells are suspended, and the collagen solution hardens together with the cells to form a collagen biomatrix with fibroblasts and neuronal cells embedded therein.

This collagen biomatrix with the cells embedded therein thus forms the dermis layer of the in vitro test tissue according to the invention.

Furthermore, in addition an epidermal layer is built up on the dermis layer. This is carried out in particular by layering the dermis with keratinocytes, which are characterized in more detail elsewhere herein. Thereby it is particularly provided that before the application of the keratinocytes, the dermal collagen matrix is firstly layered with fibronectin or a similar component, which can form the basement membrane between the dermis and the epidermal layer placed thereon. Thus a multi-layered biological in vitro test tissue, containing fibroblasts and virally infected neuronal cells as well as epithelial cells, that is, keratinocytes, is obtained.

In a special embodiment of the method, the neuronal cells are infected before being embedded into the test tissue by infection with a virus, in the invention variant described in more detail here, with the herpes simplex virus 1 (HSV1). This can be carried out in a manner known per se. A latent and reactivatable virus infection in the neuronal cells is obtained thereby. The in vitro test model in this embodiment according to the invention is thus given a latency forming neuronal component.

The latent infection can be verified by molecular biological analysis. In a preferred variant, to this end a quantitative RT-PCR is carried out. It is thereby preferably specifically tested for latency-associated transcripts (LAT genes) regulating miRNA. Of course, the verification of the provided latent virus infection is not limited to these methods.

The in vitro test tissue is firstly preferably cultivated in submerse culture in a manner known per se. This cultivation phase lasts approximately 6 days. After mechanical stabilization and/or conclusion of initial phases of the build up of intact tissue layers through the introduced cells, this is followed by a cultivation in the so-called airlift culture (airlift phase). The airlift phase lasts for approximately 14 to 15 days. During the airlift phase, preferably the hornification of the keratinocytes (epidermis) is promoted, in particular by means of calcium-rich medium.

The subject matter of the invention is also a biological in vitro test tissue, which can be produced or preferably is directly produced by means of the production method described herein. The invention does not rule out further processing steps to provide the usable in vitro tissue.

For the production of the in vitro test tissue and for the use thereof according to the invention, particularly in connection with the screening of active ingredients, the invention provides that a specific reactivation of the virus infection takes place in the latently virally infected neuronal cells. In a particular embodiment this is carried out by exposure at least once, preferably twice, with at least one reactivating stressor. Preferably, this stressor is selected from energy-rich electromagnetic radiation, in particular UVB radiation (UVB exposure) and/or thermal action (heat exposure). The possibilities of the reactivation of the viral infection are not limited to these stressors. Further stressors that can be used alternatively or additionally for the purpose of the invention for virus reactivation are chemical agents, cellular messenger substances, in particular neurotransmitters and neuroindicators, changes in the ion composition of the medium, in particular depolarizing ion changes, pH value change and the reduction of the oxygen partial pressure during cultivation.

Preferably, there is a period of about 24 hours between a first and a second exposure. In particular, the time of the final (for example, second) exposure is in the range of at least 7 hours and in particular up to 25 hours before the conclusion of the cultivation phase, that is, before the fixing of the test tissue. In a special variant, an exposure of the tissue with UVB light (312 nm) with approx. 1500 mJ preferably twice for respectively 6 to 10 min takes place for reactivation. The first exposure takes place in particular 28 to 34 hours before fixing, the second exposure takes place in particular 5 to 9 hours before fixing.

The subject matter of the invention is also a method for finding (screening) an active ingredient with anti-viral action and for the selection thereof from a group of substances to be examined. In a first step, the in vitro test tissue according to the invention is provided with virally infected neuronal cells integrated therein. In a further step, the latent virus infection of the neuronal cells is specifically reactivated.

In a further step, the in vitro test tissue is brought into contact with the substance (potential active ingredient) to be tested for the antiviral property. The bringing into contact takes place in a first variant even before the specific virus reactivation. In an alternative variant, this bringing into contact does not take place until after the specific virus reactivation.

In a further step, the extent of the virus activation is tested, thereby in particular the reduction of the extent of the virus activation after bringing the in vitro test tissue into contact with the substance to be tested compared to the virus activation of a parallel control batch, which was not brought into contact with the substance to be tested, indicates an antiviral effect of the substance. Alternatively, the reduction of the viral load by the substance to be tested can be compared to a control batch, wherein a known active ingredient with an anti-viral action was used as comparison active ingredient. Known active ingredients, for example, virustatics such as aciclovir, can be applied as a control.

In a following step, the substance that can thus be characterized as having an antiviral action is identified and/or selected and provided from the group of the substances to be tested, optionally automatically.

The substance to be tested in a first variant of the invention is applied topically to the in vitro test tissue. Through topical application active substances that can be used in particular therapeutically on the skin surface can be tested or identified in vitro reproducibly and under standardized conditions. In an alternative variant, the substance to be tested is applied into the culture medium surrounding the test tissue.

In one variant, the substance to be tested is brought into contact with the in vitro test tissue following the reactivation of the virus, namely preferably in a period of 2 to 7 days, preferably 2 to 4 days, after the virus reactivation. In an alternative variant, bringing the test tissue into contact with the substance to be tested already takes place before or, alternatively or additionally, in the course of the induction of the reactivation. The addition of the substance can already take place from day 1 of the cultivation phase of the test tissue in the airlift culture.

To verify the extent of the virus activation, the invention provides in a first assay to carry out a quantitative RT-PCR. Specifically virus-relevant gen expressions are thereby tested in a manner known per se. In an alternative assay, an immunohistochemical staining with in particular HSV1 specific antibodies is carried out. In a special embodiment these are polyclonal anti-HSV1 antibodies. The immunohistochemical staining is carried out in a manner known per se and can optionally be quantified in a manner known per se. If the test tissue is thereby cultivated in multiwall plates, for example, the staining can be automatically quantified directly in the test tissue preparation microscopically and/or densitometrically.

The invention is characterized in more detail by the following examples and figures, without these being understood to be restrictive.

BRIEF DESCRIPTION OF DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
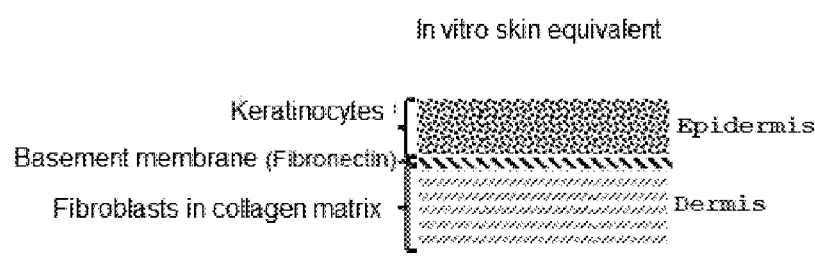
FIG. 1: Diagrammatic representation of the structure of the three-dimensional in vitro skin equivalent, composed of an epidermis layer with keratinocytes and a dermis layer with fibroblasts embedded in a collagen biomatrix. Between the epidermis and the dermis a basement membrane forms (fibronektin).
Figure 2:
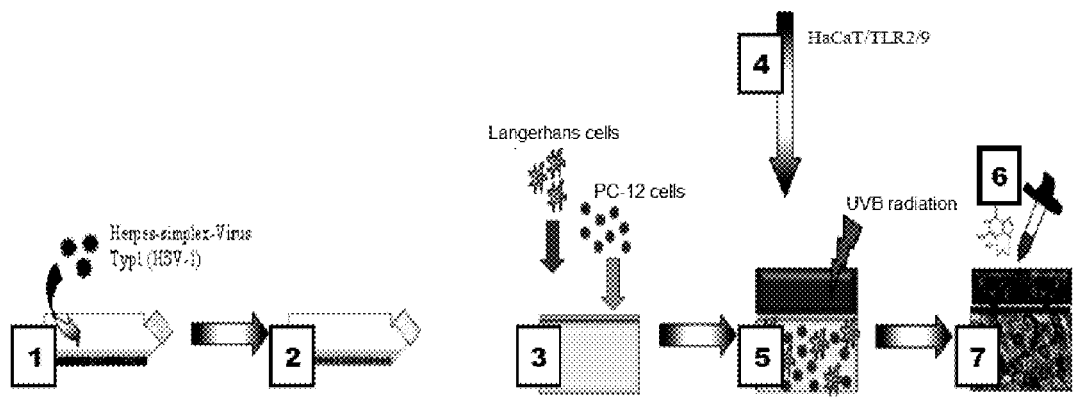
FIG. 2: Specific embodiment of the method for producing an in vitro test system for testing viral infections and for screening active ingredients: in a first step (1) a neuronal cell line (PC-12) is infected with HSV1; a latent infection develops (2). The latently infected PC-12 cells are integrated into the dermis layer (3), optionally together with immunocompetent Langerhans cells. For the complete buildup of the 3D tissue, after the application of a fibronectin layer, immortalized modified keratinocyte cell line, for example, HaCaT/ΔTLR2/ΔTLR9, are applied to the dermis layer in order to form an epidermis layer (4). Through UVB radiation (312 nm, 1500 mJ, 8 min, for example twice at an interval of 24 hours), the specific virus reactivation takes place in the intePC-12 cells (5). The active virus infection occurring as a result of the reactivation and the starting intercellular communication can be modified by bringing into contact with antiviral active ingredients (6). The viral load in the tissue is then subsequently determined by means of histological staining (7).
Figure 3:
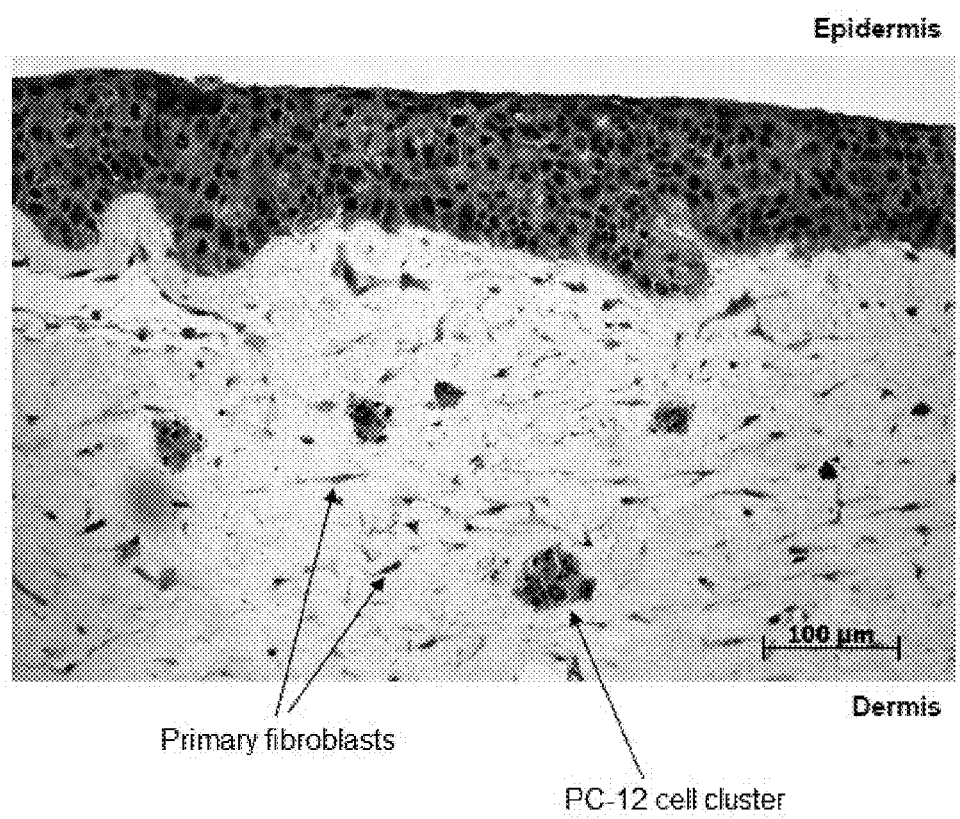
FIG. 3: Histological cross section of an in vitro test system according to the invention (HE staining) with dermis layer (light) and epidermis layer (dark) above it. Primary fibroblasts and PC-12 cells (cluster) are embedded in the dermis layer.

Example embodiments will now be described more fully with reference to the accompanying drawings.

Exemplary Embodiment

For the infection of the neuronal PC-12 cell line, the cells are seeded in a depression of a 6-well plate and incubated with the herpes simplex virus strain HF (ATCC, VR260) with a viral load of 1 PFU/cell for two hours at 37° C. Subsequently all virions not absorbed are removed by washing multiple times with buffer (PBS). The cells are cultivated for another 24 hours with fresh medium.

To develop a latent HSV 1 infection, the cells are subcultivated several times (2 to 4 passages). Before the integration into the in vitro test model, a check is carried out that no more virus activity is detectable. To this end, before each passage approx. 1 mm culture supernatant is held back and the degree of infection (TCID50) is determined using a cell-based test assay with Vero (B) cells. With this method of end dilution, the dilution stage of the material to be tested in which an infection takes place is determined. Several dilution stages are hereby prepared in parallel and it is determined at which dilution 50% of the inoculated cell cultures are infected. To detect the latent infection, alternatively the method of in situ hybridization is used. Latency-associated transcripts (LAT) are detected thereby.

The buildup of the in vitro test tissue is carried out according to a protocol optimized for the embedding of the PC 12 cells: fundamentally, the buildup is carried out in two steps. In a first step, the dermal part of the test tissue is built up, wherein primary fibroblasts as well as PC-12 cells latently infected with HSV1 are integrated into a collagen matrix with type 1 collagen. To this end, respectively $0.25 \times 10^6$ ml fibroblasts and $0.14 \times 10^6$ ml latently infected PC-12 cells are resuspended free from bubbles in a freshly produced solution of collagen I and the suspension is transferred into an insert of a 24-well plate.

In a second step, the layering of the dermis with human keratinocytes ($0.4 \times 10^6$ per ml) takes place, which then form the epidermal layer. Before the application of the keratinocytes, the dermal collagen matrix is layered with fibronectin, which then forms the basement membrane. As a negative control, a skin equivalent with non-infected PC 12 cells is built up as test tissue.

In a further assay, an immunocomponent, in particular Langerhals cells, is integrated into the test model. In a first assay, before seeding of the keratinocytes the immune cells are seeded on or in the biomatrix, in a further assay thereof, immune cells are seeded on or in the biomatrix during or following the seeding of the keratinocytes.

The buildup of the in vitro test tissue covers a total of about 21 days. The test tissue goes through different cultivation phases during this time. In the first six days, the so-called submerse phase, the tissue is cultivated completely covered with medium. Subsequently, a 14-day to 15-day airlift phase follows, wherein the test assays are carried out on the tissue. After the conclusion of the cultivation phase, the test tissue is fixed in a manner known per se optionally in Bouin's fixative solution or by means of Histofix® and subsequently preferably embedded in paraffin. In a manner known per se tissue sections are produced and a hematoxylin and eosin staining (HE) and additionally or alternatively specific antibody staining are carried out in a manner known per se according to standard protocols.

Figure 4A:
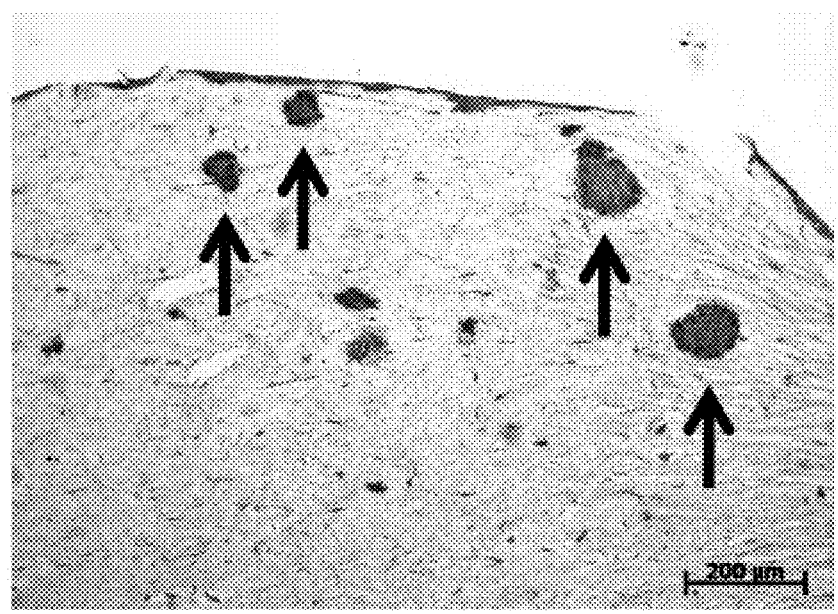
FIG. 4AB: Antibody-stained cross sections of the skin models according to FIG. 3 for the specific detection of PC-12 cells (FIG. 4B) as well as the isotype control (FIG. 4A); primary antibody: anti-tyrosine hydroxylase (abcam), dilution 1:400, as well as IgG2a isotype control (Dako), dilution 1:400; secondary antibody: anti-mouse (Dako).
Figure 4B:
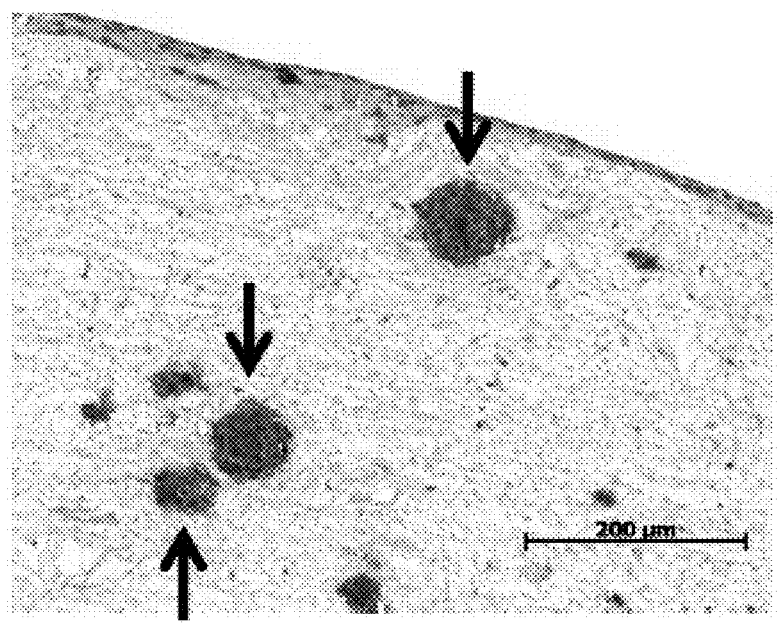
Figure 5A:
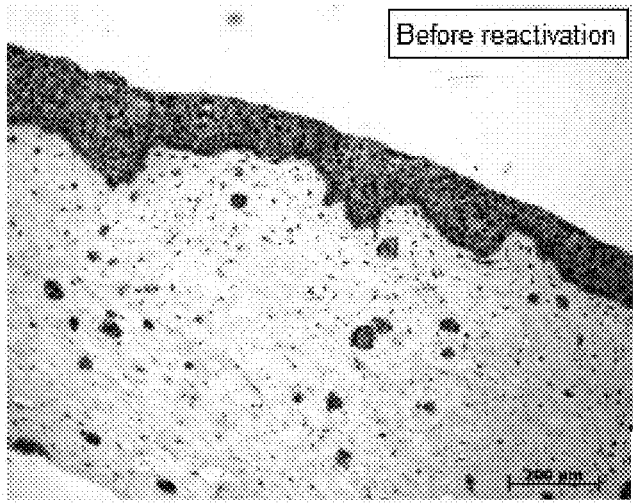
FIG. 5ABCD: Antibody-stained cross sections of the skin models according to FIG. 3 for the specific detection of HSV1. Before (FIG. 5A, FIG. 5B and FIG. 5G) as well as following a UVB exposure twice for activation, namely 55 hours and 29 hours (FIG. 5C, FIG. 5D and FIG. 5H) or 31 hours and 7 hours (FIG. 5E and FIG. 5F) before the end of the cultivation; primary antibody: polyclonal anti-HSV 1 (Biogenex), dilution 1:300; secondary antibody: anti-mouse (Dako).
Figure 5B:
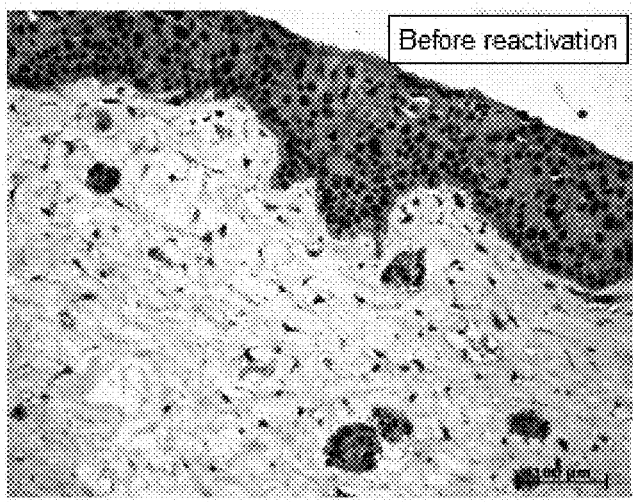
Figure 5C:
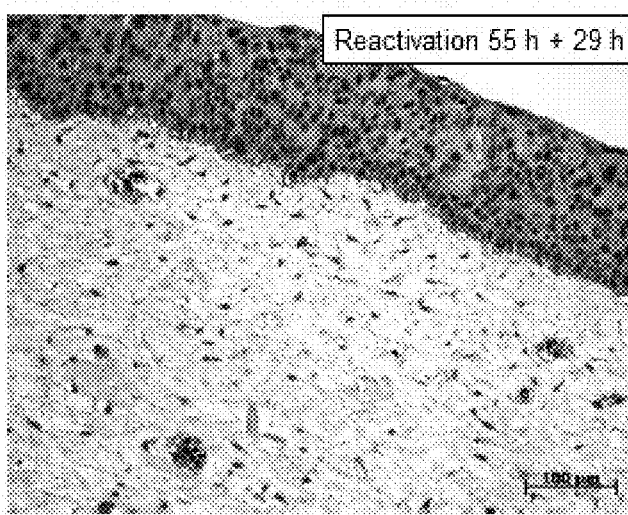
Figure 5D:
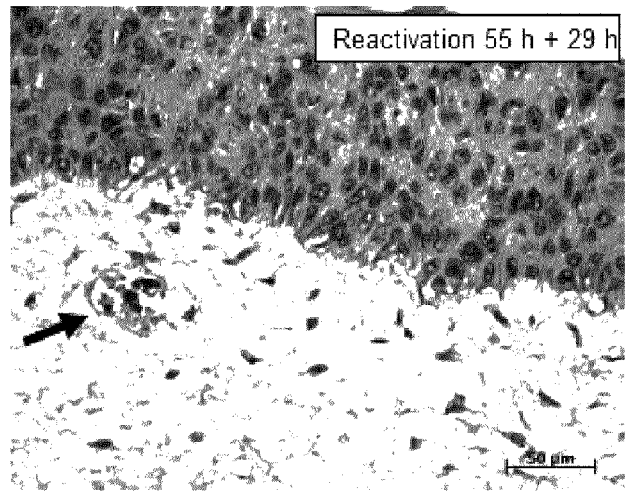
Figure 5E:
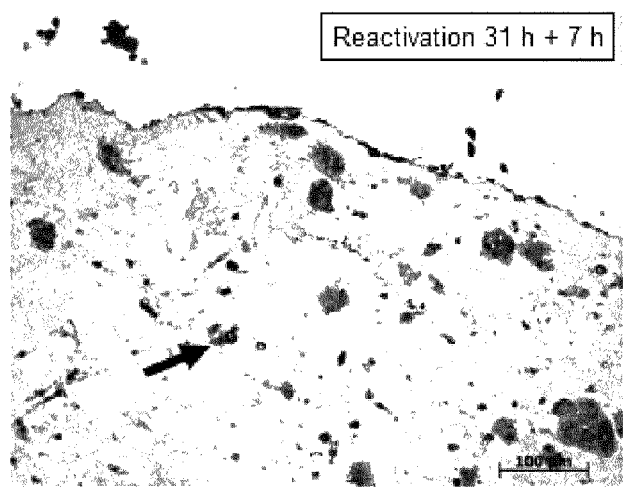
Figure 5F:
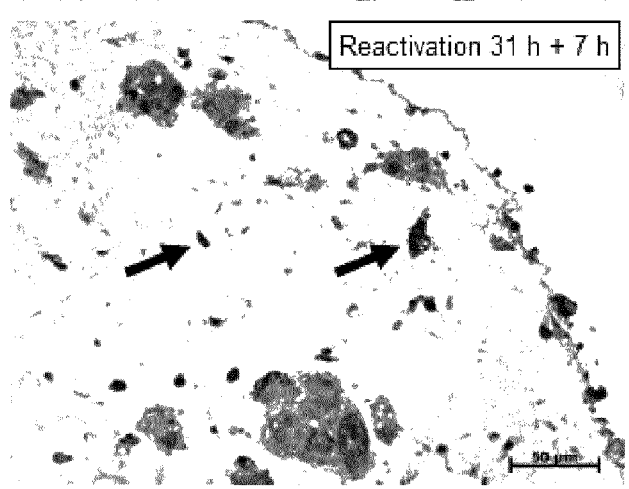

The results of the embedding of the PC-12 cells are shown in FIGS. 4 and 5. The embedded PC-12 cells can be shown in the dermis tissue in particular by histological HE staining as well as by specific antibody detection.

The specific virus reactivation is carried out in a period of at least 7 hours up to a maximum of 25 hours before the end of the cultivation phase, that is, the fixing of the tissue. For specific virus reactivation, the tissue is exposed to UVB radiation. Radiation is carried out at a wavelength of 312 nm and an energy equivalent of 1500 mJ respectively for 8 minutes. The radiation is repeated at an interval of approx. 24 hours.

In an alternative assay, the in vitro test tissue is produced with keratinocytes from the HaCaT cell line instead of primary keratinocytes. These HaCaT cells are genetically modified in the form of knock down cell lines: HaCaT/TLR2Δ and HaCaT/TLR9Δ. With the aid of these knock down cell lines, the role of the respective TLR in the scope of an HSV infection can be studied in more detail.

To test antiviral active ingredients, a "time and dose response" analysis is carried out, with the aid of which the concentration-dependent cytotoxicity and the antiherpetic effect of the individual substance can be examined. The application of the substance to be tested is carried out optionally topically in powder form or dissolved in airlift medium from day 0 of the airlift phase. Parallel thereto, a control batch is cultivated analogously with a control substance known to have an anti-viral action (Aciclovir; 50 μmol/l).

The subsequent immunohistochemical staining with an antibody specific for HSV1 shows the viral load in the microscopic investigation. By comparison of the staining in the control batch, an evaluating statement on the effectiveness of the substance concretely studied can be made.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A multi-layered biological in vitro tissue comprising:
   a dermis layer containing a collagen biomatrix with fibroblasts embedded therein; and
   an epidermis layer containing epithelial cells;
   wherein the dermis layer includes latently virally infected neuronal cells that are integrated at least into the dermis layer, and wherein the in vitro tissue is assembled from isolated cell lines and cultivated in culture medium.

2. The tissue according to claim 1, wherein the neuronal cells are selected from the group consisting of: pheochromocytoma cells type PC12 and cells derived therefrom.

3. The tissue according to claim 1, wherein the viral infection is an activated or reactivatable latent infection with herpes simplex virus type 1 (HSV1).

4. The tissue according to claim 1, wherein the epithelial cells are selected from primary keratinocytes.

5. The tissue according to claim 1, wherein the epithelial cells are selected from keratinocyte cell lines.

6. The tissue according to claim 5, wherein the epithelial cells are the keratinocyte cell line HaCaT or are cells derived therefrom.

7. The tissue according to claim 5, wherein the epithelial cells are selected from genetically modified keratinocytes that are deficient for one or more pattern recognition receptors (PRR).

8. The tissue according to claim 7, wherein the pattern recognition receptor is selected from the group consisting of: TLR2, TLR5 and TLR9.

9. The tissue according to claim 1, further comprising immunocompetent cells integrated at least into the dermis layer.

10. The tissue according to claim 9, wherein the immunocompetent cells are selected from the group consisting of Langerhans cells and cells derived therefrom.

11. The tissue according to claim 1, wherein the fibroblasts are selected from primary fibroblasts.

12. The tissue according to claim 1, wherein the collagen biomatrix is composed of native collagen type I.

13. A method for producing a multi-layered biological tissue, comprising:
    providing a multi-layered tissue containing a dermis layer comprising a collagen biomatrix with fibroblasts embedded therein and an epidermis layer containing epithelial cells;
    seeding latently virally infected neuronal cells in vitro on the multi-layered biological tissue so that the neuronal cells are integrated at least into the dermis layer of the biological tissue;
    wherein the in vitro tissue is assembled from isolated cell lines and recultivated cells from a human donor; and
    wherein the in vitro tissue is cultivated in culture medium.

14. The method according to claim 13, wherein the neuronal cells are pheochromocytoma cells type PC12, or cells derived therefrom.

15. The method according to claim 13, comprising infecting the neuronal cells before seeding by infection with herpes simplex virus type 1 (HSV1), in order to generate a latent and reactivatable virus infection.

16. The tissue according to claim 1, further comprising a layer of fibronectin positioned between the dermis layer and the epidermis layer.

17. The tissue according to claim 1, wherein collagen biomatrix comprises type 1 collagen from rat tails, the fibroblasts are isolated and recultivated from a human donor, and the epithelial cells are selected from the group consisting of recultivated keratinocytes from a human donor, a keratinocyte cell line, and a genetically modified keratinocyte cell line.

18. The tissue according to claim 1, wherein the culture medium comprises a factor selected from the group consisting of TGF-α, GM-CSF, IL-1a, and mixtures thereof.

19. A multi-layered biological in vitro tissue comprising:
    a dermis layer including a type I collagen biomatrix, fibroblasts, and PC12 cells latently infected with herpes simplex virus type 1 (HSV1), wherein the collagen biomatrix is from rat tail, and the fibroblasts are recultivated fibroblasts isolated from a human donor;
    an epidermis layer including epithelial cells selected from the group consisting of recultivated keratinocytes from a human donor, an immortalized keratinocyte cell line, and a genetically modified keratinocyte cell line; and
    a basement membrane positioned between the dermis layer and the epidermis layer,
    wherein the in vitro tissue is assembled and maintained in cell culture medium.

20. The tissue according to claim 19, wherein the HSV1 can be reactivated by application of a stressor selected from the group consisting of UVB radiation exposure, heat exposure, chemical agents, neurotransmitters, neuroindicators, ion composition changes, pH changes, changes in oxygen partial pressure, and combinations thereof.

* * * * *